United States Patent [19]

Siretchi et al.

[11] Patent Number: 4,784,643
[45] Date of Patent: Nov. 15, 1988

[54] DETECTOR OF AIR BUBBLES IN A CIRCUIT OF LIQUID

[75] Inventors: Roman Siretchi, Pau; Pierre Vignacq, Soustons, both of France

[73] Assignee: Societe Anonyme: M.M.S., France

[21] Appl. No.: 54,968

[22] Filed: May 28, 1987

[30] Foreign Application Priority Data

May 28, 1986 [FR] France ................................ 86 07657

[51] Int. Cl.$^4$ .............................................. A61M 5/14
[52] U.S. Cl. ...................................... 604/122; 604/65
[58] Field of Search ................... 604/122, 123, 65, 66, 604/67

[56] References Cited

U.S. PATENT DOCUMENTS

| | | | |
|---|---|---|---|
| 4,447,191 | 5/1984 | Bilstad et al. ................... | 604/122 X |
| 4,525,163 | 6/1985 | Slavih et al. ........................... | 604/65 |
| 4,673,927 | 6/1987 | Cianciaricchia et al. ........ | 604/65 X |

*Primary Examiner*—Edward M. Coven

*Attorney, Agent, or Firm*—Lowe, Price, LeBlanc, Becker & Shur

[57] ABSTRACT

First and second spaced apart optical emitter-receiving pairs are located along a liquid carrying conduit. A regulator circuit is coupled to each emitter-receiver pair to control the operation of that pair inside a maximum response range regardless of the transparency of the liquid. The regulator circuit is so arranged as to supply the emitter with a voltage which is a function of the difference between a voltage supplied by the receiver portion of an optical-receiver pair and a reference voltage. A differential circuit produces a differential signal representing the difference between the signals produced by the receiver portions of the optical emitter-receiver pairs and a comparator circuit is connected to the differential circuit in order to generate an alarm signal as a function of the differential signal. The detector is particularly useful as an air bubble detector in a transfusion or perfusion system, and can also provide a container-empty alarm in such systems.

4 Claims, 1 Drawing Sheet

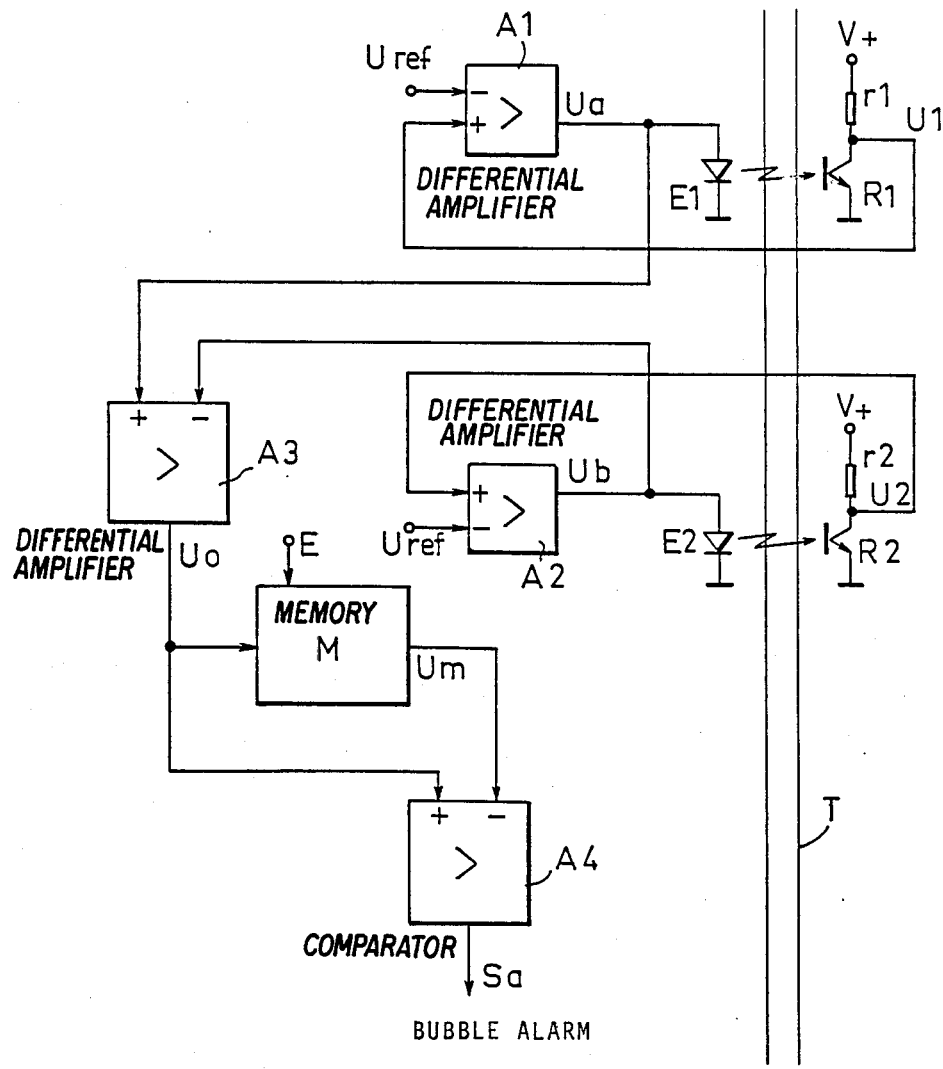

DETECTOR OF AIR BUBBLES IN A CIRCUIT OF LIQUID

FIELD OF THE INVENTION

The present invention relates to an air bubble detector or, more generally, to a detector of liquid discontinuity in a circuit of liquid. More particularly, the invention relates to an air bubble detector, of the type comprising photoemissive means and photoreceptor means adapted to be placed on two opposite sides of a conduit carrying the liquid, and means for processing the signals produced by the photoreceptor means in order to produce an information signal in response to the appearance of an air bubble or a discontinuity of liquid in the conduit at the detector level.

The invention is particularly, but not exclusively, applicable to the detection of air bubbles in a circuit of liquid in parenteral nutrition or blood transfusion systems, as well as to bottle-empty detection in such systems.

BACKGROUND OF THE INVENTION

In parenteral nutrition or blood transfusion systems, the liquid supplied from a bottle is injected into a patient by means of a pump. Air may be introduced into the circuit of liquid, for example if the pump continues to work when the bottle is empty, or through a leak in the parenteral perfusion or transfusion tube due to the exerted pumping forces. Because of the danger that they represent for the patient, the air bubbles must be detected.

The use of an air bubble detector, incorporated in the perfusion or transfusion tube, is impossible from a practical and economical standpoint. Indeed, the tube must be sterilizable as well as readily dismountable and reassembled; in addition, the detector must not transmit any electrical current to the patient's body via the liquid which may be very conducting; finally, the tube being a consumer good, its cost must remain as low as possible.

It is therefore important to use air bubble detectors which are external to the perfusion or transfusion line, which makes the detection rather difficult, all the more so that the liquids can be of very varied types with completely different characteristics.

Among the known air bubble detectors, some are of optical type with a photo-emitter and a photo-receptor, disposed in facing relationship on two opposite sides of a conduit in transparent material carrying the liquid. The passage of an air bubble causes a variation in the transparency of the medium situated between the photo-emitter and the photo-receptor, hence a variation which can be detected from a signal supplied by the photo-detector.

Use of these known detectors raised difficulties due to the very wide dispersion of the transparency of the liquids normally carried in the conduit; transparent, translucid or opalescent liquids.

In order to overcome these difficulties, it has been proposed to use air bubble detectors of optical type in which the reference value, as a function of which the variation of the signal produced by the photo-detector is analyzed, is pre-adjusted manually. But, the detector adjusted in this way, is only capable of operating correctly inside a limited range of liquid transparency. Moreover, an error of adjustment may always occur, with serious consequences.

It has also been proposed in French patent application No. 2 361 644, to use a plurality of optical emitter-receiver pairs, one of which is used to make an automatic adjustment or pre-conditioning of the detector, making a distinction between transparent liquid and opaque liquid. The fact remains that, for every system of operation ("transparent" liquid or "opaque" liquid) the range of transparency remains wide, which always makes it difficult to select a reference value. Moreover, this automatic adjustment can be performed at the cost of a rather great complexity of the detector.

SUMMARY OF THE INVENTION

It is therefore the object of the invention to propose an air bubble or liquid discontinuity detector capable of working reliably within a wide range of liquid transparency, without the need of making any adjustment as a function of the liquid used, and with a structure which is kept relatively simple.

This object is reached with a detector of the type defined at the start of the present description and in which, according to the invention:

the photo-emissive and photo-receptor means comprise first and second optical emitter-receiver pairs designed to be placed apart one from the other along a conduit, and a regulator circuit operationally coupled to each emitter-receiver pair for controlling the operation of said pair inside a maximum response range, independently of the transparency of the liquid, said regulator circuit being so arranged as to supply the emitter with a voltage which is a function of the difference between a voltage supplied by the receiver and a reference voltage, and the processing means comprise a differential circuit, arranged so as to produce a differential signal representing the difference between the signals produced by the receivers and a comparator circuit connected to the differential circuit in order to supply or not, an informative signal as a function of the differential signal.

The combination of the differential detection with the automatic control of the sensitivity at its maximum value makes it possible here to work inside a wide range of liquid transparency, in the best possible conditions, and without requiring any special pre-adjustment as a function of said transparency. The result is a greater reliability of operation of the air bubble detector, which is particularly important in an application to perfusion or transfusion systems.

In addition, the detector according to the invention can be used to detect air bubbles in a conduit carrying a liquid, as well as to detect that a reservoir or bottle supplying a circuit of liquid is empty, emptying of the conduit on which the detector is mounted being, for said detector, equivalent to the appearance of an air bubble.

Thus, the detector according to the invention can be used, in particular, for detecting when a bottle is empty in perfusion and transfusion systems. In this particular application, the detector according to the invention offers many advantages over the known bottle-empty detectors. The latter are generally optical type devices designed to monitor the flow of the liquid in the drip chamber; the detector is energized every time a drop passes and a bottle-empty alarm signal is given when the time interval between two drops exceeds a predetermined threshold. However, the system is then sensitive to the liquid supply flow since the frequency of the drops varies with the flow rate. Moreover, positioning of the detector with respect to the drip chamber is not precise and readily disturbed. Also, the emitter and receiver are relatively far apart since the drip chamber has a diameter of several centimeters, hence the possibility of unwanted conditions due to changes in the environment lighting (sunlight, artificial light, etc.). The use of a detector according to the invention, at the level of the conduit supplying the drip chamber, eliminates all the aforesaid drawbacks: detection is insensitive to the flow rate and to the nature of the fluid, and it is not affected by any changes in the ambient lighting since the distance between the associated emitter and receiver is only of a few millimeters.

BRIEF DESCRIPTION OF THE DRAWING

The invention will be more readily understood on reading the following description with reference to the accompanying drawing, in which the one and only FIGURE is a diagram of one embodiment of the detector according to the invention.

DETAILED DESCRIPTION OF A PREFERRED EMBODIMENT

As illustrated in the FIGURE, the detector according to the invention is operationally coupled to a conduit or tube, such as for example a tube forming part of a parenteral nutrition or blood transfusion system in which the liquid is administered to a patient by means of a pump, such as a peristaltic-type pump. The detector is then placed on a tube situated downstream of said pump.

The detector comprises two optical emitter-receiver pairs, E1-R1 and E2-R2 respectively. In each pair, the emitter E1, E2 and the corresponding receiver R1, R2 are placed in facing relationship, on either side of tube T, outside of and close to the transparent wall thereof. The two pairs E1-R1, E2-R2 are separated by a distance for example equal to a few millimeters.

The pairs E1-R1 and E2-R2 are preferably identical. Emitters E1, E2 are for example light emitting diodes emitting in infra-red, whereas receivers R1, R2 are phototransistors sensitive to the radiations emitted by said diodes. The emitter-collector circuit of each transistor R1, R2 is series-connected with a resistor r1, r2 between the ground and a terminal of voltage V+ of a supply source. Voltages U1, U2 drawn between the ground and the collectors of transistors R1, R2 constitute the output signals thereof, the amplitude of which signals varies as a function of the intensity of the received light.

Diodes E1, E2 are supplied with voltages Ua, Ub from differential amplifiers A1, A2. Said amplifiers A1, A2 have their negative inputs connected with a terminal of reference voltage level Uref, their positive inputs being connected to the collectors of transistors R1, R2 to receive voltages U1, U2 respectively.

Voltages Ua and Ub are also applied to the positive and negative inputs of a differential amplifier A3 which delivers a differential signal Uo. Said latter is applied to the input of an analog memory M, such as a capacitor circuit, for storing the amplitude of the differential signal Uo in response to the application of a control signal on a storage control input E in memory M. In parallel, the differential signal Uo is applied continuously on an input of a comparator A4, of which the other input receives the stored value Um of signal Uo outputted from memory M. Comparator A4 delivers an alarm signal Sa when the difference between signals Uo and Um exceeds a predetermined threshold.

As a variant, a digital-type memory M can be used. In this case, the signal Uo is converted to digital form at the output of amplifier A3, and comparator A4 is in digital circuit form.

The detector described hereinabove works as follows:

In every emitter-receiver pair, when the transparency of the liquid varies, a corresponding variation of the voltage supplied by the phototransistor occurs, which variation results in a modification of the voltage applied to the light emitting diode, i.e. a modification of the emitting energy. For example, if the transparency diminishes, the amplitude of the signal produced by the phototransistor reduces, but the diode supply voltage increases due to an increase in the difference between the reference voltage Uref and the voltage supplied by the phototransistor. It becomes possible then to keep the phototransistor working inside a linear range of maximum sensitivity in order to preserve an optimum detection sensitivity. In other words, feedback of the signal supplied by each detector on an input of the differential amplifier which supplies the voltage to the corresponding emitter, enables the control of the response of the emitter-receiver pair in order to keep its sensitivity to the maximum value.

Differential amplifier A3 supplies a differential signal Uo which is proportional to the difference between signals Ua and Ub, hence representative of the difference between voltages U1 and U2.

In the absence of air bubbles in tube T, the transparencies of the media situated in the fields of action of the emitter-receiver pairs are identical. Signal Uo has a low if not nil amplitude. If the emitter-receiver pairs on the one hand, and amplifiers A1 and A2 on the other hand, have identical or very close characteristics, the appearance of an air bubble at the level of an emitter-receiver pair will therefore cause an important increase in the amplitude of signal Uo in absolute value.

However, it is not really necessary to have emitter-receiver pairs or amplifiers A1, A2 with identical characteristics since the air bubble detection is achieved by monitoring the amplitude variations of signal Uo and not by comparing the instant absolute value of said signal with a threshold value.

Thus, after a predetermined interval following the detector start-of-operation, such as for example around ten seconds, the value of signal Uo is stored in memory M by sending a storage control signal on input E. Throughout the remainder of the operation, the stored value Um is used a reference value to detect a variation of instant signal Uo which is such that the difference Uo−Um exceeds a predetermined threshold. Such a variation will then be ascribed to the presence of an air bubble and will cause the triggering of an alarm signal.

As already indicated, the detector can also be used for detecting the emptiness of a bottle in a perfusion or transfusion system. In this case, the emptying of the tube at detector level is equivalent to the passage of an air bubble. The detector then has to be placed on a tube downstream of the bottom and upstream of the drip chamber.

The invention is not in any way limited to the description given hereinabove, and on the contrary covers any modification that can be brought thereto without departing from its scope.

What is claimed is:

1. A detector for detecting air bubbles or other liquid discontinuities in a circuit of liquid, comprising:
   first and second spaced apart optical emitter-receiver pairs spaced apart from each other along a conduit carrying said liquid, each emitter-receiver pair comprising a light emitting means and a light receiving means placed in a facing relationship on opposite sides of said conduit;
   a regulating circuit having a first input connected to said light receiving means, a second input of said regulating circuit connected to a source of a reference voltage and an output of said regulating circuit connected to said light emitting means in order to supply said light emitting means with a voltage which is a function of the difference between a voltage supplied by said light receiving means and said reference voltage such that said emitter-receiver pairs operate throughout a predetermined response range, independently of transparency of said liquid;
   processing means comprising a differential circuit including first and second inputs connected to said first and second emitter-receiver pair, respectively, in order to produce a differential signal representative of the difference between a first voltage supplied by said light receiving means in said first emitter-receiver pair and a second voltage supplied by said light receiving means in said second emitter-receiver pair; and
   said processing means operative to generate an alarm signal upon the appearance of an air bubble or liquid discontinuity in said conduit as a function of said differential signal.

2. The detector of claim 1, wherein said differential signal is proportional to the difference between the voltage supplied to said light emitting means in said first-emitter-receiver pair and the voltage supplied to said light emitting means in said second emitter-receiver pair.

3. The detector of claim 1, wherein said processing means further comprises value storage means connected to said differential circuit for storing the value of the differential signal at a given time, and further comprises a comparator circuit having inputs connected to said differential circuit and said value storage means, respectively, in order to generate said alarm signal when the difference between the current value and the stored value of said differential signal exceeds a predetermined threshold level.

4. The detector of claim 1, wherein said first and second optical emitter-receiver means, spaced apart one from the other along said conduit are located downstream from a container placed in-line with said conduit in a perfusion or transfusion installation in order to generate said alarm signal when said container becomes empty.

* * * * *